(12) United States Patent
Takei et al.

(10) Patent No.: US 6,331,276 B1
(45) Date of Patent: Dec. 18, 2001

(54) SENSOR AND MEASURING APPARATUS USING THE SAME

(75) Inventors: Hiroyuki Takei, Hiki-gun; Takeshi Sakamoto, Asaka, both of (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/313,782

(22) Filed: May 17, 1999

(30) Foreign Application Priority Data

May 19, 1998 (JP) .................................................. 10-136994

(51) Int. Cl.$^7$ .................................................... G01N 21/27
(52) U.S. Cl. ..................... 422/82.09; 422/82.11; 436/525
(58) Field of Search ............... 422/82.05, 82.09, 422/82.11; 436/523, 525, 528, 531, 532, 164; 356/301, 445

(56) References Cited

U.S. PATENT DOCUMENTS

| | | | |
|---|---|---|---|
| 4,481,091 | * 11/1984 | Brus et al. | 204/157.1 R |
| 5,023,139 | * 6/1991 | Birnboim et al. | 428/402 |
| 5,151,956 | * 9/1992 | Bloemer | 385/11 |
| 5,567,628 | * 10/1996 | Tarcha et al. | 436/525 |
| 6,180,415 | * 1/2001 | Scfhultz et al. | 436/518 |

FOREIGN PATENT DOCUMENTS

| | | |
|---|---|---|
| 798561 | 10/1997 | (EP) . |
| 2256477 | 12/1992 | (GB) . |
| WO9809153 | 3/1998 | (WO) . |

OTHER PUBLICATIONS

Journal Vacuum Science Technology, vol. B9, No. 2, Mar./Apr., 1991, "Near–field Optics: Microscopy with Nanometer–size fields" W. Denk et al, pp. 510–513.

Science, vol. 277, Aug. 22, 1997, "Selective Colorimetric Detection of Polynycleotides Based on the Distance–Dependent Optical Properties of Gold Nanoparticles", R. Elghanian et al, pp. 1078–1081.

Journal of Vacuum Science and Technology, B9, No. 2, Mar./Apr. 1991, "Near–field optics: Microscopy with nanometer–size fields", W. Denk et al, pp. 510–513.

Surface Science, 156, 1985, "Optical Absorption of Small Metallic Particles", U. Kreibig, pp. 678–700.

* cited by examiner

Primary Examiner—Jeffrey Snay
(74) Attorney, Agent, or Firm—Mattingly, Stanger & Malur, P.C.

(57) ABSTRACT

A highly sensitive sensor and measuring apparatus are provided by using a sensitive change in the reflection spectrum of metal microparticles present on a metal surface according to a change of dielectric constant in the surrounding area.

23 Claims, 11 Drawing Sheets

PRIOR ART

FIG. 2B

PRIOR ART

REFLECTANCE SPECTRA OF GOLD PARTICLES

FIG. 5

CHANGE IN REFLECTANCE SPECTRUM INDUCED BY IMMERSION IN WATER

SENSOR AND MEASURING APPARATUS USING THE SAME

BACKGROUND OF THE INVENTION

This invention relates to sensors such as an immuno sensor, gas sensor or ion sensor using surface plasmon resonance phenomenon, and to a device using these sensors.

Figure 2A:
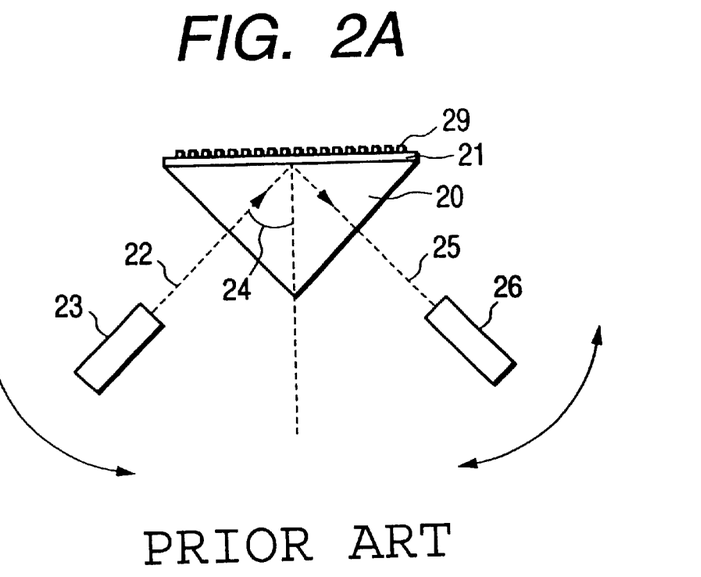
FIG. 2A is a drawing showing an apparatus according to the prior art.
Figure 2B:
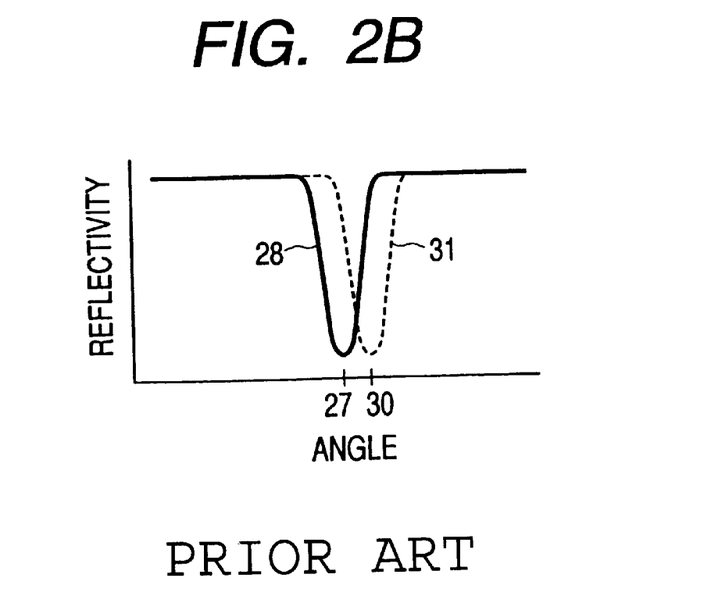
FIG. 2B is a drawing describing a measurement principle.

The surface plasmon is a propagating wave of collectively oscillating free electrons at an interface between a thin metallic film and a dielectric material. As the propagation of the wave is sensitively influenced by the dielectric constant at the interface, it forms a basis for a detection principle in immuno sensors and gas sensors. A typical structure of such a sensor is shown in FIG. 2A. A thin metallic film 21 made of free electron metal such as gold or silver with thickness of approximately 50 nm is formed on the surface of a prism with a high refractive index, and which in addition to the thin metallic film 21 has a molecule recognition layer 29. To generate the surface plasmon at the surface of the thin metallic film 21, the film 21 must be irradiated from the prism side by p polarized collimated monochromatic light 22 from a light source 23 at a particular angle called resonance angle. Generation of the surface plasmon is monitored by detecting specularly reflected light 25 with a detector 26. In other words, as shown in FIG. 2B, when the incident angle matches the resonance angle 27 at which the surface plasmon is excited, the intensity 28 of the reflected light becomes extremely small because a large portion of the energy in the incident light becomes transferred to the surface plasmon. The resonance angle depends on the dielectric constant at the surface; when change in the dielectric constant is induced at the surface of the thin metallic film 21, the intensity 31 of the reflected light now decreases at a new resonance angle 30. Because the resonance angle depends only on the dielectric constant within the region of several hundreds of nm from the surface, adsorption of a small amount of sample is enough to shift the resonance angle. Now if a device is constructed with a molecule recognition layer 29 capable of recognizing and binding a specific molecule, and if a sample fluid is allowed to flow over the surface, the dielectric constant will vary if a specific molecule in the sample fluid is bound. Hence, by observing the light reflected around the resonance angle, it can immediately be known if the specific molecule has been captured by the molecule recognition layer 29.

In order to make use of the surface plasmon phenomenon associated with a thin metallic film, apart from the above collimated monochromatic light, a method (1) is known where the film is irradiated by divergent monochromatic light and the reflected light is measured by a light sensor array, and a method (2) where the film is irradiated by collimated white light, and the reflected light is measured by a spectrometer. In both methods it is the dependence of the resonance angle for light of a specific wavelength on the dielectric constant of the interface which is used.

SUMMARY OF THE INVENTION

In the measuring apparatus using surface plasmon resonance phenomenon of the prior art, the relative position of the light source, thin metallic film, and light detector must be accurately held as well as smoothly driven mechanically when required. To improve measurement accuracy, it is desirable to increase the distance between the thin metallic film and the light detector, but this precludes compact construction of the apparatus. Further, as the surface plasmon resonance method is sensitive to temperature, temperature control or correction for a drift in temperature is required, which also prevents the apparatus from being made compact. Another optical phenomenon associated with a free electron metal is localized surface plasmon. When particles made of a free electron metal, such as gold particles, are irradiated with white light, free electrons in the particles are induced to collectively oscillate within the confine of the particles at a certain frequency. This type of collective oscillation does not propagate, thus known as localized surface plasmon.

The plasmon resonance wavelength is known to depend on the dielectric constant in the near-field optical region within several fractions of a particle diameter away from the particle surface, and a method of detecting biological molecules using this technique is also known (Science, 277, 1078, 1997).

In principle, it is possible to enhance the near field intensity by changing the shape of the gold particles to an ellipsoid (Surface Science, 156, 678, 1985). It is also known that the strong near field intensity is generated around the end of a sharp metal tip when positioned in the vicinity of a metal substrate and irradiated (J. Vac. Sci. Technol., 9, 510, 1991).

Based on the idea that sharp tips and elongated particles have the same effect, the inventor found that when cap-shaped gold particles were formed near a metal substrate, much stronger coloration than that associated with the gold particles of the prior art was observed. Enhanced coloration implies that the near field intensity around the surface adsorbed cap-shaped gold particles is rather enhanced. Thus, a device based on the principle of simply measuring change in the absorption spectrum induced by adsorption of molecules on the particle surface within the near field can be simpler and more compact than a conventional surface plasmon sensor. This invention aims to provide a sensor and a measuring apparatus which is compact and easy to handle, and which is based on the coloration change of the new particles.

DESCRIPTION OF THE PREFERRED EMBODIMENTS

Figure 3A:
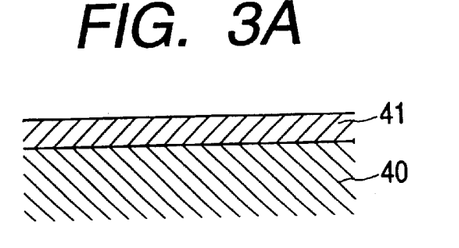
FIG. 3A–FIG. 3D are drawings showing a procedure for forming metal particles on a thin metal film comprising a sensor according to this invention.
Figure 3B:
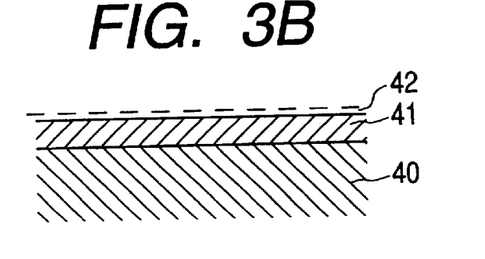
Figure 3C:
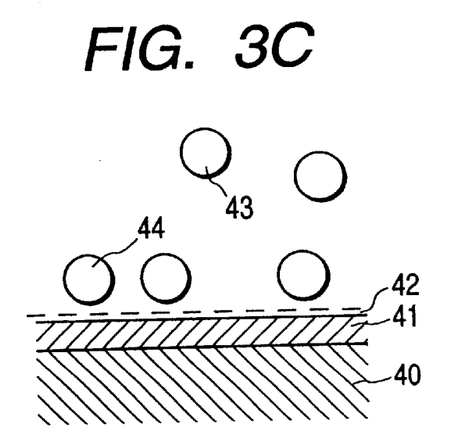
Figure 3D:
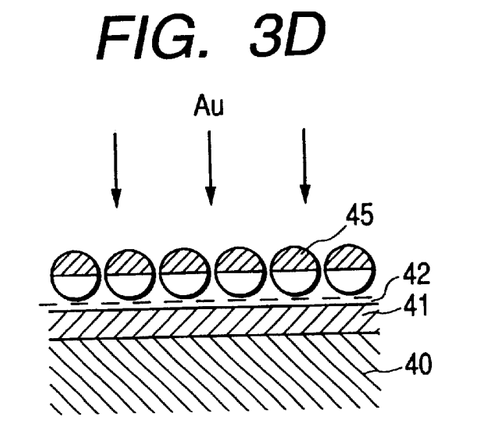

FIG. 3A–FIG. 3D are drawings showing a procedure for forming cap-shaped metal particles on a thin metal film 41 which comprises a sensor according to this invention. As shown in FIG. 3A, the thin metallic film 41 of 5 nm to 1000 nm thickness is formed by evaporating a free electron metal such as gold, silver, copper or aluminum on a transparent substrate 40. Next, as shown in FIG. 3B, this thin metallic film 41 is treated by a 10 mM solution of a thiol molecule such as 2-aminoethanethiol or thioglycolate so as to form a modified layer 42 on the surface. Next, as shown in FIG. 3C, polystyrene beads 43 of 5 nm to 100 μm particle diameter, which are suspended in a 1–50 mM carbodiimide solution, are added to the thin metallic film coating so that a single bead layer 44 is formed on the surface of the thin gold film 41 which has the modified layer 42 on its upper surface. Next, as shown in FIG. 3D, after drying and depositing gold to 5 nm to 500 nm thickness, cap-shaped gold particles 45 are formed on the surface of the polystyrene beads (Japanese Patent Laid-Open Hei 11-1703).

According to this embodiment, what is formed is not solid spherical gold particles. Rather, it is polymer particles covered by electrically isolated cap-shaped gold particles. Hereafter, however, they will be referred to for convenience as gold particles. As will be clear from the description of the following embodiment, the presence of the underlying gold substrate enhances coloration observed with substrate 40. (Japanese Patent Laid-Open 10339808A).

This coloration is due to the fact that light within a specific wavelength band is selectively absorbed by the particles when white light is irradiated onto the substrate 40 at a fixed angle, and light not absorbed is mostly reflected specularly at the substrate surface. On the other hand, as there is no wavelength dependence for transmitted light, the coloration effect is not observed in that case.

This phenomenon may be considered to be due to the interaction of the gold film and gold particles, as described hereafter. Apparently, by forming gold particles in the vicinity of the thin gold film, the propagating surface plasmon of the thin film and the localized plasmon of the particles interact with each other, thereby producing new absorption characteristics. The reflectance spectra obtained by irradiating collimated white light at a fixed angle and measuring the specularly reflected light contain sharp peaks in the ultraviolet, visible light and infrared regions, and the wavelengths of these absorption peaks depend on the type and thickness of the metal on the substrate, the diameter and adsorption density of the polystyrene beads, and the type of thickness of the metal which is thermally evaporated on the polystyrene beads. It is noted that the shape of particles is particularly important as can be seen from the fact that spherical gold particles adsorbed on a gold thin film exhibit much reduced coloration.

Figure 4:
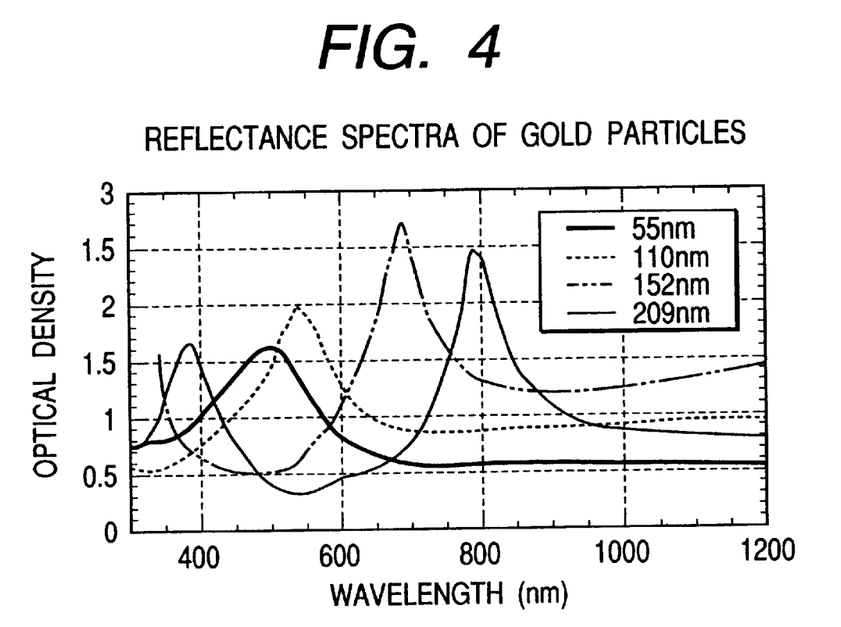
FIG. 4 is a drawing showing a reflectance spectrum of a sensor according to this invention using polymer particles of different sizes.

FIG. 4 is a drawing showing a reflection spectrum in an embodiment of the sensor according to this invention using polymer beads of different sizes. When white light is irradiated at a fixed angle to a sensor comprising polystyrene beads of 55, 110, 152 and 209 nm particle size on which 20 nm of gold are deposited, a composite of metal particles and metal film is obtained which has different reflection spectra depending on the particle size.

Figure 5:
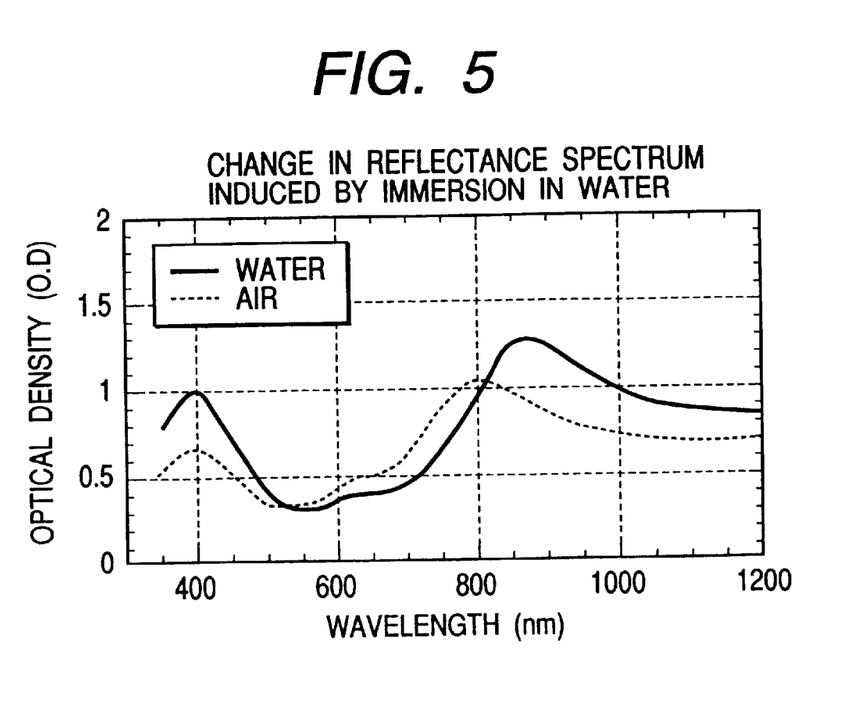
FIG. 5 is a drawing showing dependence of a reflectance spectrum on the immersion fluid according to the dielectric constant of gold particle in an embodiment of a sensor according to this invention.

FIG. 5 is a drawing showing the reflectance spectrum which depends on the dielectric constant of the media surrounding metal particles in the embodiment of the sensor according to this invention. This figure shows, as examples, measurement results for the reflectance spectrum when a sensor, comprising gold of 20 nm thickness deposited on polystyrene beads of 209 nm size, is left in air, and the reflectance spectrum when the gold particle surface of the sensor is immersed in water. From this figure, it is seen that the maximum absorbance is shifted from a wavelength of 800 nm to 870 nm by replacing the gold particle surface with water which has a different dielectric constant from that of air. The slight difference in the spectrum of the 209 nm particle diameter sensor of FIG. 4 compared to that of FIG. 5 is due to differences of measurement conditions; the latter was obtained by using an integrating sphere.

The variation in the spectrum depends on the variation of dielectric constant in a region from several nm to several 100 nm from the thin metallic film surface, and it is both rapid and reversible. This will now be described referring to FIG. 6 and FIG. 7.

Figure 6:
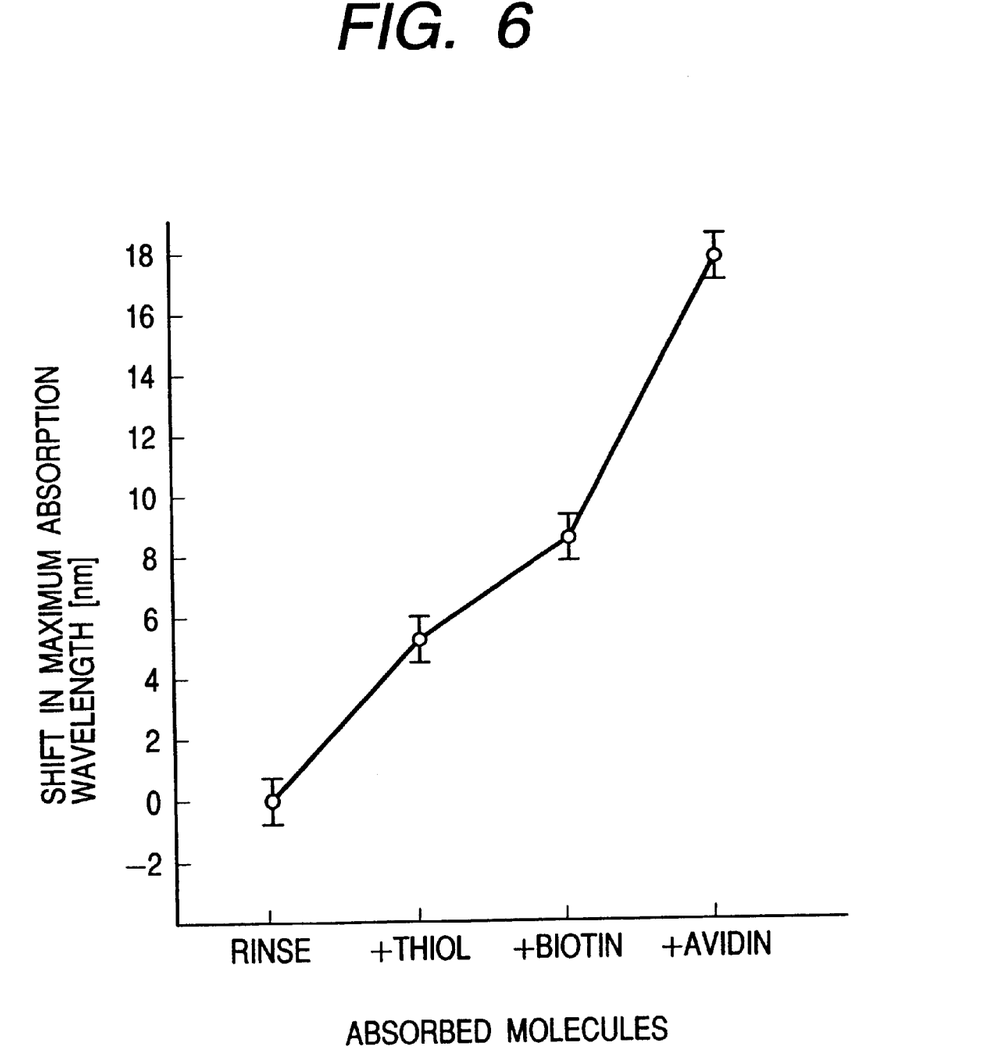
FIG. 6 is a drawing of shifts in the maximum absorption wavelength depending on surface modifications of gold particle surfaces in an embodiment of a sensor according to this invention.

FIG. 6 is a drawing showing a maximum absorption wavelength depending on the surface modification of gold particle surfaces. In the figure, the horizontal axis shows the type of molecules adsorbed on the gold particle surfaces, and the vertical axis shows the amount of total shift in the maximum absorption wavelength (amount of variation in the spectrum). This data is for the case when the gold particle size is 110 nm and light is irradiated at an angle of 0 degrees. In the case of this figure, firstly, the wavelength was examined when there was no surface modification (rinse), when thiol was adsorbed (+THIOL), when biotin was absorbed on the end of the thiol (+BIOTIN), and when avidin was absorbed on the end of the biotin (+AVIDIN).

Figure 7:
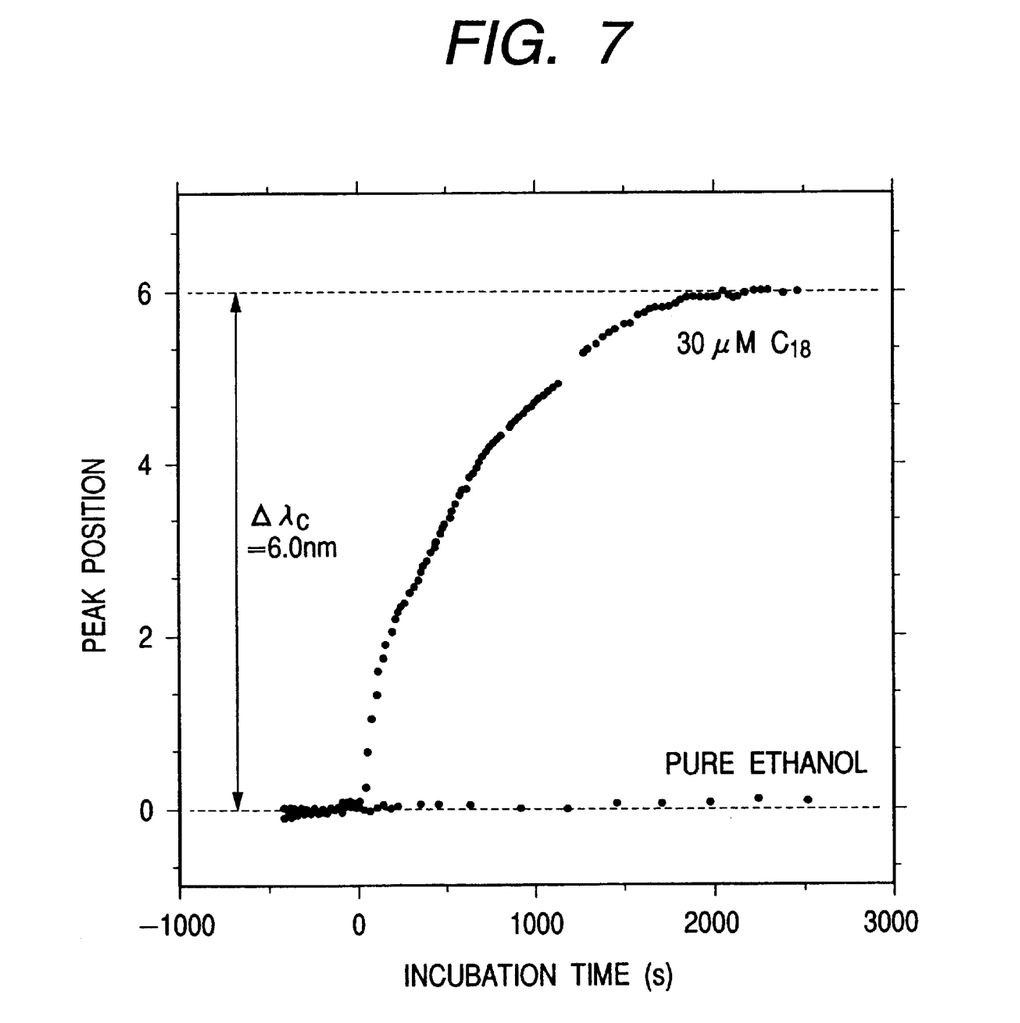
FIG. 7 is a drawing of a time course variation of the maximum absorption wavelength due to the adsorption of octadecane thiol to gold particle surfaces in an embodiment of a sensor according to this invention.
Figure 8A:
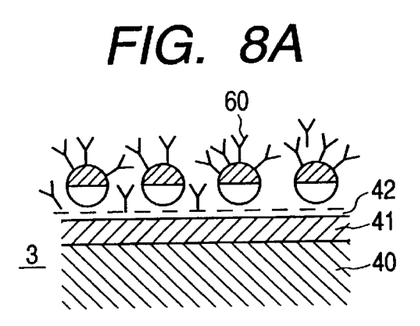
FIG. 8A–FIG. 8E are drawings showing surface modifications of gold particles in an embodiment of a sensor according to this invention.
Figure 8B:
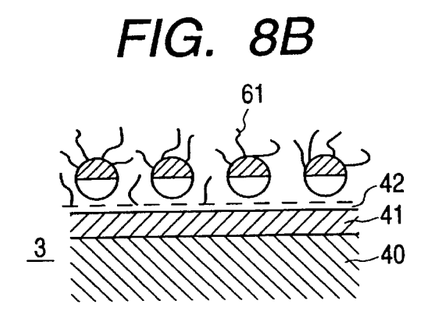
Figure 8C:
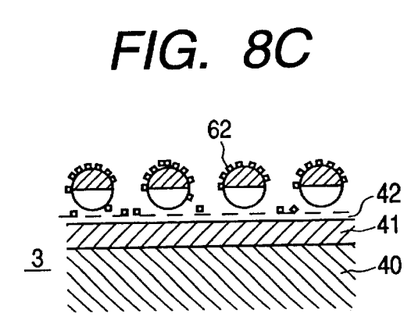
Figure 8D:
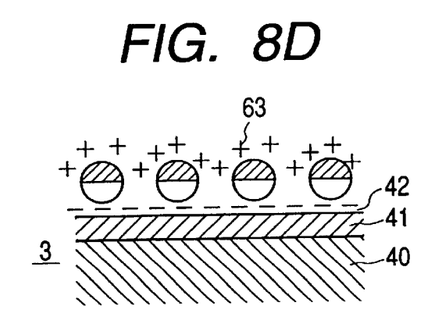
Figure 8E:
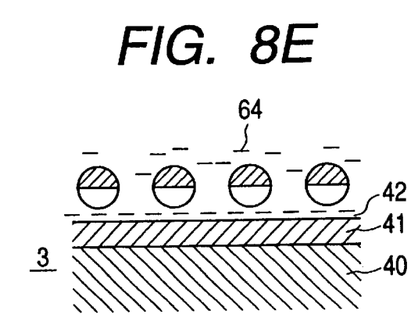

FIG. 7 is a figure showing an example of a time course change in the maximum absorption wavelength due to the adsorption of octadecane thiol on the gold particle surface in a sensor according to an embodiment of this invention. The maximum absorption wavelength of gold particles remains constant when immersed in pure ethanol, but if octadecane thiol (concentration 30 um in ethanol) is added at time=0, the absorption peak wavelength begins to change. After 2500 seconds, the maximum absorption wavelength shows a total shift of 6 nm. Octadecane thiol is known to form a dense, single molecular layer known as a self-assembled monolayer on gold surfaces, therefore the above data shows that the sensor of this invention has sufficient sensitivity to detect the formation of a single molecular layer, and that the required response is obtained within 100 seconds.

Further, according to this invention, the sensor surface consists of a monolayer of polymer beads adsorbed on a gold surface; each polymer bead is furthermore covered by a cap-shaped gold particle. Due to the interaction of the localized surface plasmon of the gold particles and the propagating surface plasmon of the thin gold film, a sensitive sensor wherein the absorption spectrum largely varies due to the change of dielectric constant in an enhanced electric field can be realized as shown by the calculation of the preceding paper, J.Vac.Sci.Technol., 2,510,1991.

EMBODIMENT I

Figure 1:
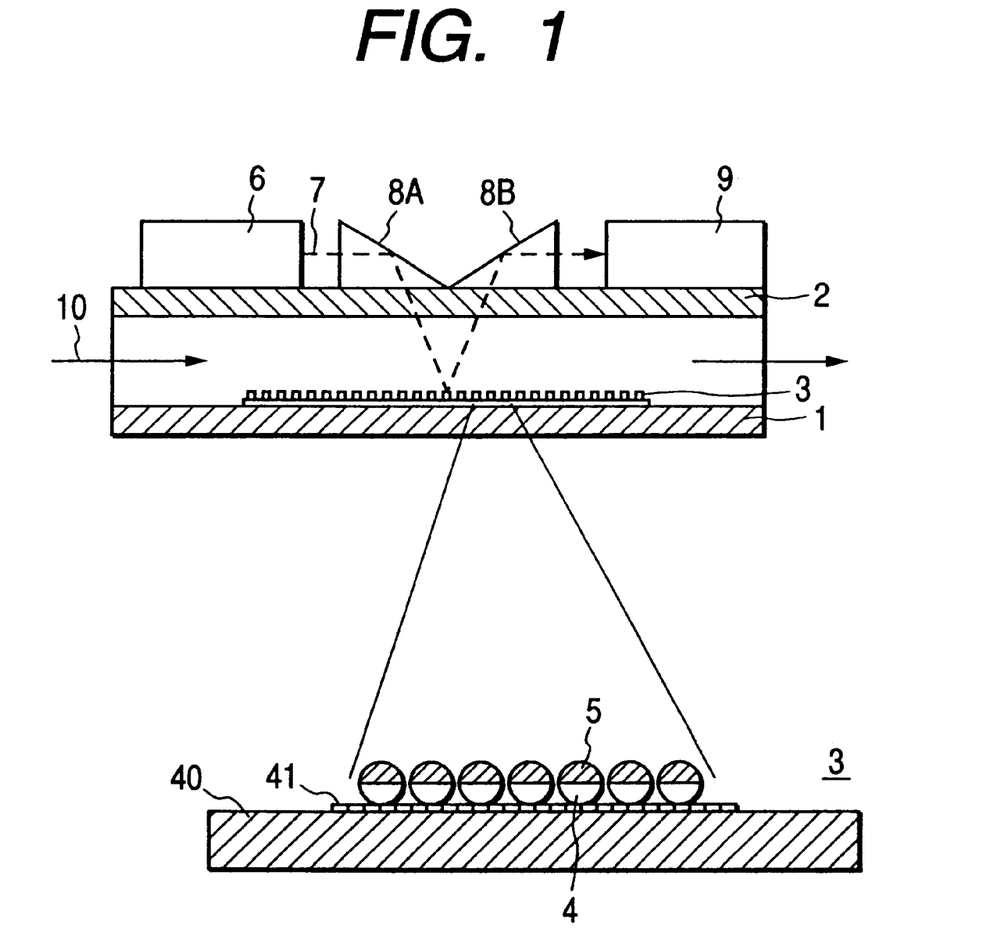
FIG. 1 is a sectional view showing one embodiment of the measuring apparatus of this invention.

An example of the measuring apparatus of this invention is shown in FIG. 1. The apparatus comprises a fluid channel with a metal plate 1 and transparent substrate 2 arranged on either side, and a composite 3 of a thin metal film 41 and gold microparticles 5 is thermally evaporated on the metal plate 1. In the figure, a modifying film 42 is omitted. The composite 3 has a structure wherein gold 5 is thermally evaporated to a thickness of 5 nm to 1000 nm on polystyrene beads of size 5 nm to 100 um prepared by the procedure described in FIG. 3. The substrate 40 of the composite 3 may be the metal surface 1, but is preferably transparent as described in FIG. 3. It is convenient if the substrate 40 can be readily removed from and attached to the transparent substrate 2 so as to allow rapid exchange in accordance to change in the object being measured.

Various modifications may be made to the gold particle surfaces of the composite 3, typical modifications being shown in FIG. 8. In FIG. 8A–FIG. 8E, as described in FIG. 3, 40 is the transparent substrate, 41 is the thin metallic film thermally evaporated on the substrate, and 42 is the modifying layer which is formed on the thin metallic film 41. 8A shows the case where the surface of the gold microparticles of the composite 3 is modified by an antibody 60, 8B shows the case where the surface of gold microparticles of the composite 3 is modified by a nucleic acid 61, 8C shows the case where the surface of the gold microparticles of the composite 3 is modified by zeolite 62, 8D shows the case where the surface of the gold microparticles of the composite 3 is modified by a cation exchanger 63, and 8E shows the case where the surface of the gold microparticles of the composite 3 is modified by an anion exchanger 63.

According to this embodiment, monochromatic light 7 from a light source 6 is led into the fluid channel via the transparent substrate 2 in an optical system 8A, reflected at the surfaces of the gold microparticles of the composite 3, and detected by a detector 9 in an optical system 8B. If a sample fluid 10 which is led into the fluid channel contains a target molecule for which detection the surface of the gold microparticles has been modified, this is selectively adsorbed. As changes in the reflectance of the reflected monochromatic light 7 are very sensitive to the state of the surfaces of the gold microparticles of the composite 3, the presence of the target molecule can be detected.

EMBODIMENT II

Figure 9:
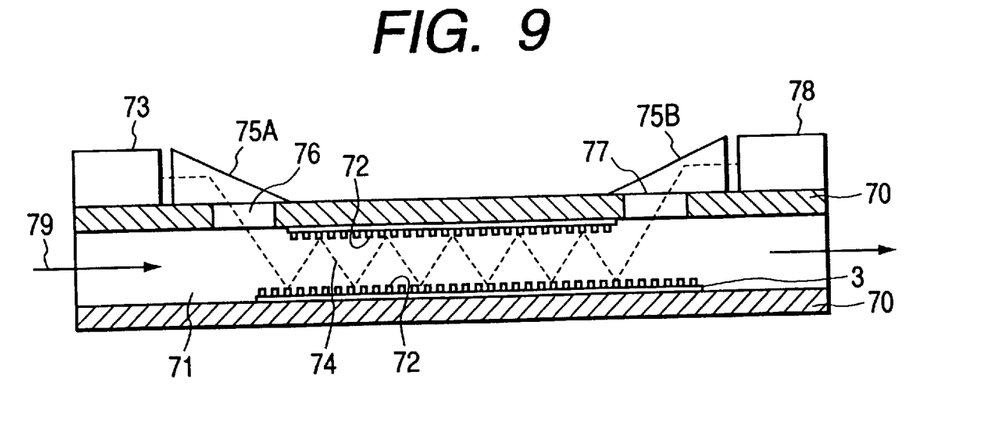
FIG. 9 is a sectional view showing another embodiment of the measuring apparatus according to this invention.

Another embodiment of the invention is shown in FIG. 9. Here, a fluid channel 71 is provided with upper and lower metal plates 70. A composite 72 of the thin metallic film 41 and gold microparticles is formed on the surface of the metal plate 70 above and below the flowpath 71. In this example also, the modifying layer 42 has been omitted. The substrate of the composite 72 may be the metal plate 70, but is preferably the transparent substrate 40 as was shown in FIG. 3. Specifically, as in the embodiment of FIG. 1, it is convenient if this is provided as standard for the sensor, and replaced according to the change in the object being measured. Various modifications may be made to the surface of the composite 72, such as the examples shown in FIG. 8A–FIG. 8E.

According to this embodiment, monochromatic light 74 from a light source 73 is led to the composite 72 on the metal plate through a transparent window 76 by an optical system 75, and after multiple reflections at the upper and lower composites 72, it passes through a transparent window 77 where it is led to a detector 78 by the optical system 75, and detected. If a sample fluid 79 which is led into the fluid channel 71 contains a target molecule corresponding to a surface modification of the gold microparticles of the composite 3, this is selectively adsorbed. As changes in the reflectance of the reflected monochromatic light 7 are very sensitive to the state of the surfaces of the gold microparticles of the composite 3, the presence of the specimen can thus be detected.

In this embodiment, the monochromatic light 74 is led to the detector 78 after multiple reflections at the upper and lower composite 72, so the presence of the target molecule can be detected with a higher accuracy.

EMBODIMENT III

Figure 10A:
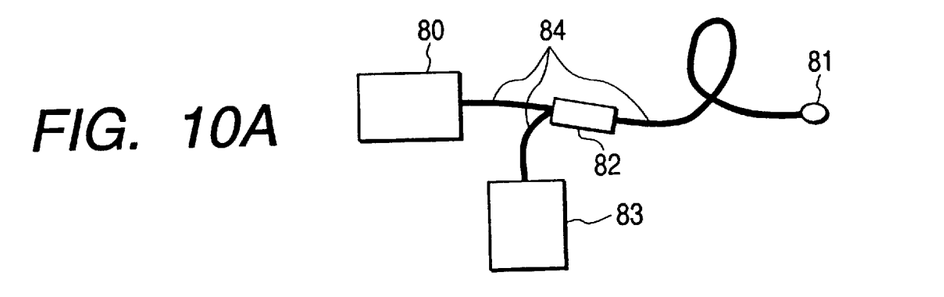
FIG. 10A–FIG. 10C are schematic drawings showing another embodiment of the measuring apparatus according to this invention.

Another embodiment of the invention is shown in FIG. 10A. The apparatus comprises a light source 80, an optical fiber 84 connected to the light source 80, a sensing head 81 connected to the optical fiber 84, an optical fiber 84 joined to the optical fiber 84 via a coupler 82, and a detector 83 connected to this.

Figure 10B:
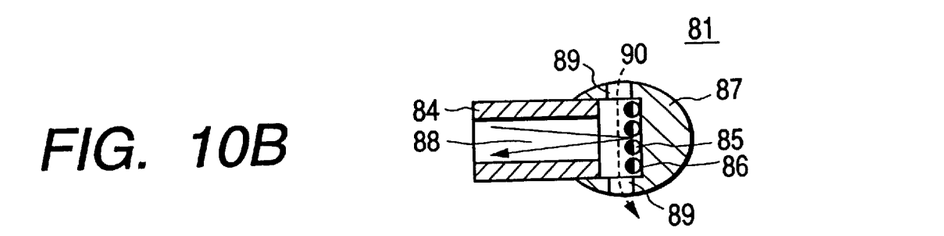

The detailed construction of the sensing head 81 is shown in FIG. 10B. The sensing head 81 is a chamber having a hollow part which fits onto the tip of the optical fiber 84, and a composite 85 of the thin metallic film 41 and gold microparticles is formed on an inner surface 86 of the hollow part of the chamber. Light propagated from the optical source 80 via the optical fiber 84 is irradiated onto the composite 85, and partially reflected as reflected light 88 by the composite 85. The reflected light 88 is led to the detector 83 by the coupler 82, and detected. A hole 89 for introducing the sample fluid is provided in the chamber 81. A sample fluid 90 is introduced via the hole 89 as shown by the dotted line. Various modifications may be made to the surface of the composite 85 as in the previous embodiments, and a target molecule contained in the sample fluid introduced from the hole 89 can be adsorbed on the surface according to the modification of the composite 85. If adsorption occurs at the surface of the composite 85, the reflectance of the monochromatic light 88 varies with high sensitivity, so the presence of the target molecule in the sample fluid 90 can be detected.

According to this embodiment, a fiber is used, and since a fiber can be inserted into a narrow detecting space, various applications are possible. If the sensing head 81 is replaced for each subject being measured, contamination can be prevented.

Figure 10C:
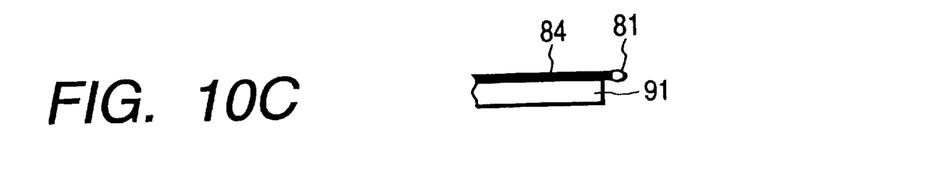

Further, the fiber 84 and sensing head 81, whereof only the tip is shown in FIG. 10C, may be formed in one piece with an endoscope 91 for examining living organisms. In this apparatus, a specific position in a subject can be examined by the endoscope, and a particular specimen examined at this position. In this case, although not shown in the figure, the control functions normally performed by an endoscope can be used to control the opening and closing of the hole 89 which is used to introduce sample fluid.

EMBODIMENT IV

Another embodiment of this invention will be described referring to FIGS. 11A–11D and FIGS. 12A–12D.

Figure 11A:
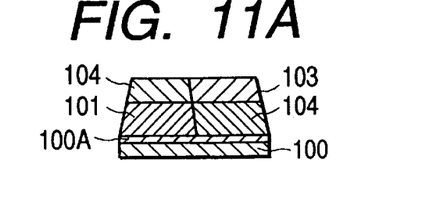
FIG. 11A–FIG. 11D are drawings describing another embodiment of the measuring apparatus according to this invention.

First, a thin gold film 100A of 5 nm to 100 nm thickness was formed by thermal evaporation on a flat silicon substrate 100. To render the surface of the thin gold film hydrophilic, the film was chemically modified by a thiol molecule layer 42 by treating it with a thiol solution with a carboxylic or amino terminal group such as thioglycolate or 2-aminoethanethiol. Next, polystyrene beads of 5 nm to 100 um particle diameter suspended in a carbodiimide solution of concentration 0.01M to 1M were brought into contact with the thin metallic film surface 100A of the substrate 100 so as to form a monolayer of polystyrene beads on the thin metallic film surface. Polystyrene beads of different sizes were adsorbed in different areas 101, 102, 103 and 104. Next, gold was thermally evaporated to a thickness of from 5 nm to 100 nm on the adsorbed polystyrene beads. In this way, a sensor surface comprising gold particles of different sizes in four regions was formed as shown in FIG. 11A.

Figure 12A:
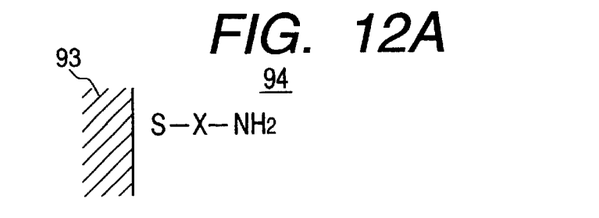
FIG. 12A–FIG. 12E are drawings showing a method for biomolecular modification of gold surfaces using the binding of thiol molecules to gold.
Figure 12B:
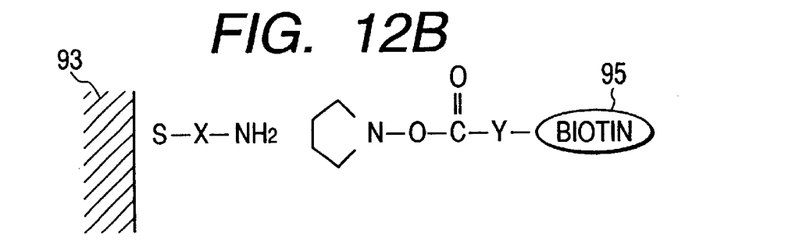
Figure 12C:
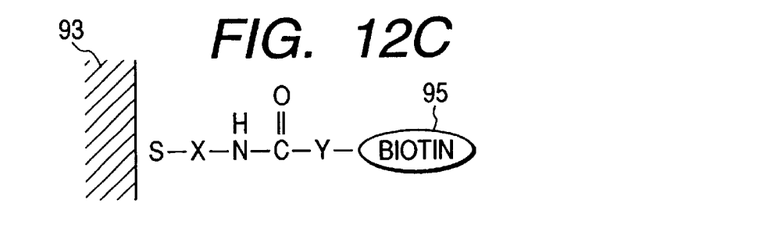
Figure 12D:
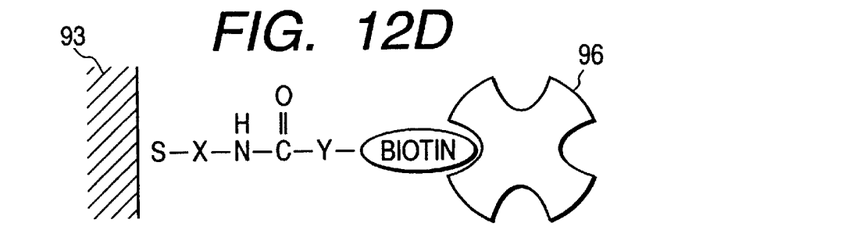
Figure 12E:
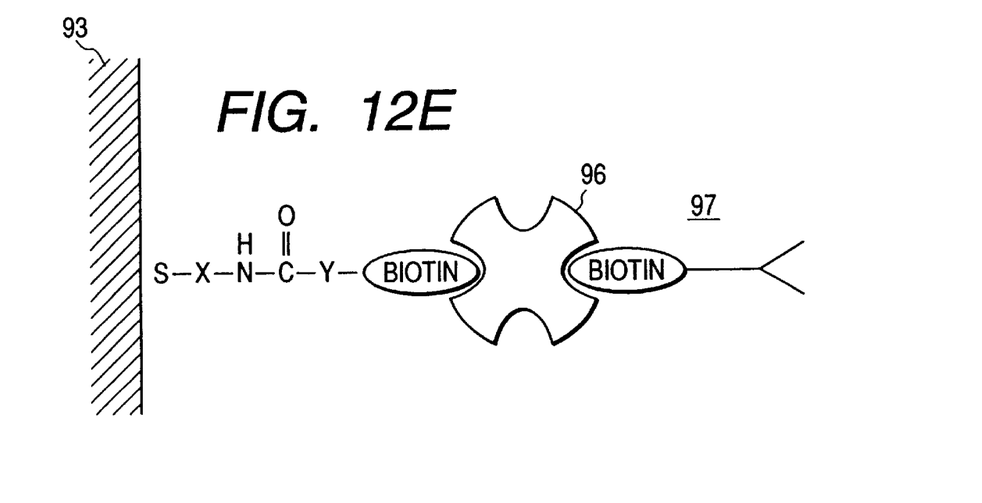

The surface of the gold microparticles in this embodiment was chemically modified by using gold-thiol chemistries. A surface 93 of the gold microparticles was immersed in a 10 mM aqueous solution of thiol molecules 94 having an amino group such as aminoethanethiol so as to modify the surface 93 of the particles with an amino group, as shown in FIG. 12A. Next, biotin 95 modified by N-hydroxysuccinimide suspended in a buffer solution of pH 7–9 was activated by carbodiimide, and added to the gold microparticles previously modified by an amino group, as shown in FIG. 12B. As a result, a peptide bond is formed between the carbonylic carbon and the amino group so as to modify the surface of the gold microparticles with biotin. Next, avidin or streptoavidin 96 comprising four binding sites was bound to the biotin, as shown in FIG. 12D. Next, any biotinylated biological molecule 97 such as protein, ligand or DNA can be bound to the surface of the avidin modified gold microparticles, as shown in FIG. 12E.

Figure 11B:
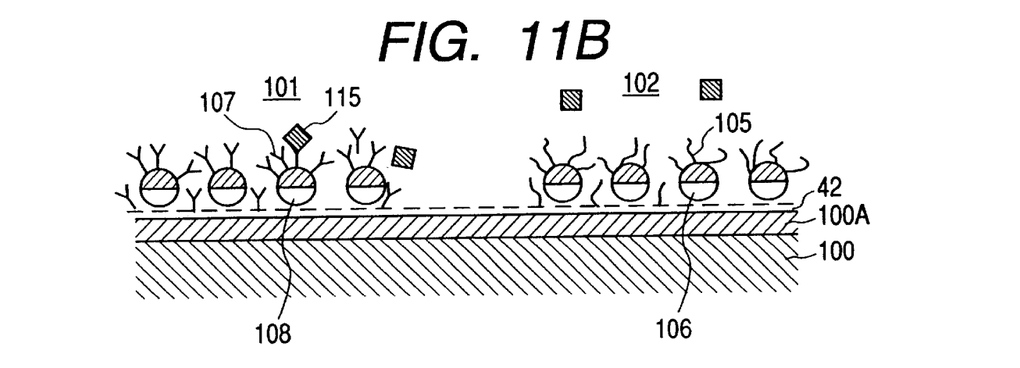

As an example of this surface modification, in FIG. 11B, gold microparticles 108 chemically modified by an antibody 107 are formed in a region 101, and gold microparticles 106 chemically modified by a ligand 105 are formed in a region 102.

Figure 11C:
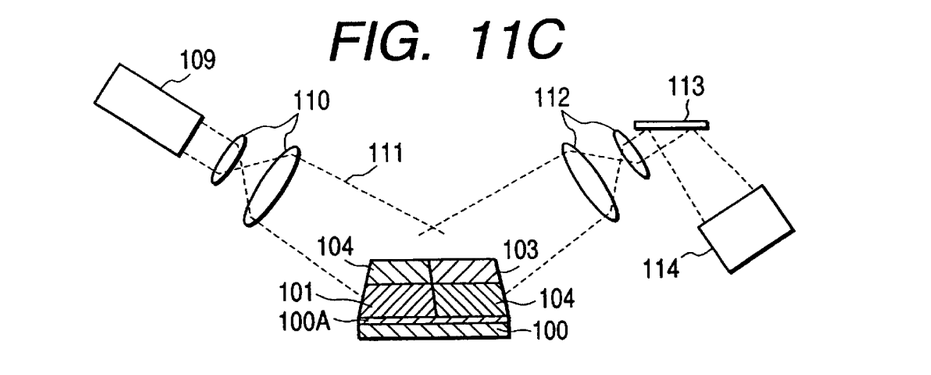

As shown in FIG. 11C, the silicon substrate 100 comprising the modified gold microparticles is irradiated at a fixed angle by a light source 109. Collimated white light 111 from a collimator 110 is specularly reflected, collected by an optical system 112, split spectrally by a diffraction grating 113 and detected by a detector 114.

A liquid comprising a specimen 115 is led onto the silicon substrate 100, and if the specimen 115 is selectively bound only by the antibody 107 in the region 101 for example, only the wavelength of the absorption peak 116 specific to the region 101 varies, and so the specimen 115 can be identified by monitoring the spectral variation.

Figure 11D:
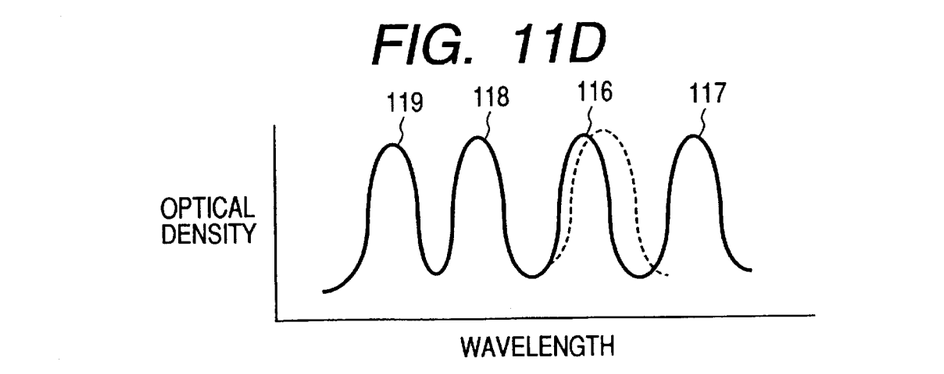

FIG. 11D schematically shows an example of this spectral variation. It is seen that of the spectrum peaks 116–119 detected from the regions 101–104, only the spectrum peak 116 in the region 101 to which the specimen 115 is bound, varies as shown by the dotted line.

According to this embodiment, if plural regions are formed on one substrate and each of these is suitably modified, a plurality of specimens in one sample solution may be simultaneously detected, so the time dependent variation described in FIG. 7 may be reduced to 1/number of regions for each specimen.

EMBODIMENT V

Figure 13A:
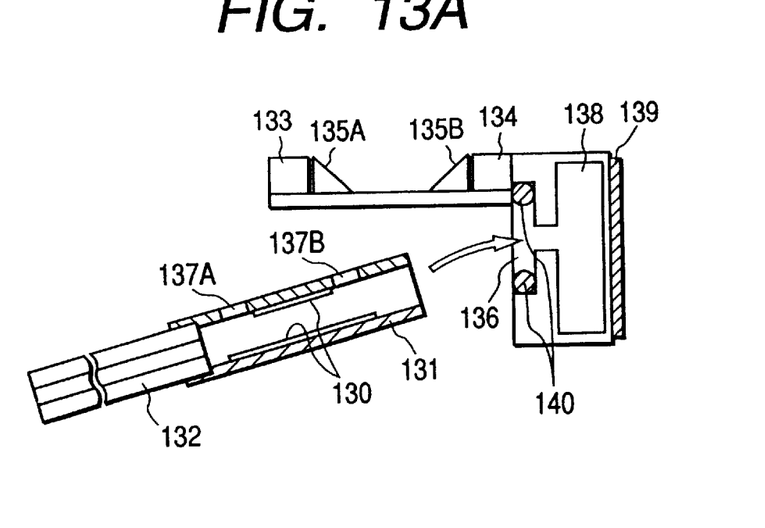
FIG. 13A and FIG. 13B show a sectional view and the overall aspect of another embodiment of the measuring apparatus according to this invention.
Figure 13B:
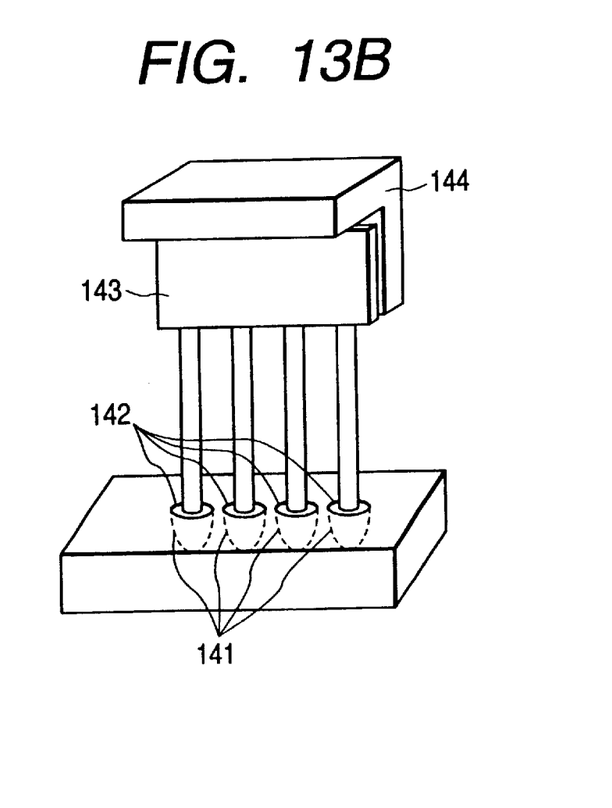

A further embodiment of this invention is shown in FIGS. 13A and 13B. The basic construction of this embodiment is identical to that described in FIG. 9, but in order to eliminate sample cross-contamination when measuring a large number of samples, a structure is adopted wherein a sensor part and an optical detecting part can be separated and the sensor part can be freely attached or detached, as shown in FIG. 13A, thus permitting easy replacement.

In the sensor part, a composite 130 of gold microparticles and a thin metallic film is formed in a micro fluid channel 131 into which a microcapillary 132 is inserted. In addition to a light source 133, optical system 135A, 135B and optical detector 134, the optical detecting part comprises structural parts for joining the sensor part to the optical system. When the sensor part is inserted in a joining hole 136 of the optical detecting part, light from the light source 133 passes through an optical window 137A of the sensor part to irradiate the composite 130. The reflected light passes through an optical window 137B, and is detected by an optical detector 134. 140 is a packing to prevent leakage of sample fluid.

The optical detecting part comprises a mechanism for aspirating sample fluid, i.e., the joining hole 136 is connected to a chamber 138. A piezo device 139 is fitted to the chamber 138. By applying a pulse voltage to the piezo device, the internal volume of the chamber 138 is sharply reduced and then restored so that the pressure in the chamber 138 is reduced in a pulse-like manner, so sample solution is aspirated into the sensor part from outside.

Plural channels are formed in the sensor part 143 and optical detecting part 144, as shown in FIG. 13B, so that plural sample solutions 142 in sample solution holes 141 can be simultaneously aspirated and measured. According to this construction, if the sensor part 143 is replaced for each sample solution, errors due to cross-contamination between sample solutions are easily prevented.

What is claimed is:

1. A sensor comprising a flat substrate and a layer of insulating beads of a polymer or non-metal arranged effectively uniformly on said substrate, wherein a free electron thin metal microparticle layer is formed over substantially half the outer surface of said insulating beads on the opposite side to said substrate.

2. A sensor according to claim 1, wherein said layer of polymer or non-metal insulating beads comprise an insulating material which is a polymer including polystyrene, styrene/butadiene, polyvinyltoluene, styrene/divinylbenzene or vinyltoluene/t-butylstyrene effectively having a monodisperse diameter of 5 nm to 100 um, or a non-metal including silicon, silicon oxide, gallium arsenide or glass, and said free electron thin microparticle layer is a layer of gold, silver, copper or aluminum of 1 nm to 100 $\mu$m thickness.

3. A sensor according to claim 1, wherein said substrate surface comprises a free electron metal layer, the surface of said free electron metal layer is chemically modified by thiol, disulfide or sulfide, and said insulating beads of a polymer including polystyrene, styrene/butadiene, polyvinyltoluene, styrene/divinylbenzene or vinyltoluene/t-butylstyrene effectively having a monodisperse diameter of 5 nm to 100 um, or of a non-metal including silicon, silicon oxide, gallium arsenide or glass, are adsorbed on the surface of said free electron metal layer.

4. A sensor according to claim 2, wherein said substrate surface comprises a free electron metal layer, the surface of said free electron metal layer is chemically modified by thiol, disulfide or sulfide, and said insulating beads of a polymer including polystyrene, styrene/butadiene, polyvinyltoluene, styrene/divinylbenzene or vinyltoluene/t-butylstyrene effectively having a unique diameter of 5 nm to 100 um, or of a non-metal including silicon, silicon oxide, gallium arsenide or glass, are adsorbed on the surface of said free electron metal layer.

5. A sensor comprising a flat substrate and a layer of insulating beads of a polymer or non-metal arranged effectively uniformly on said substrate, wherein a free electron thin metal microparticle layer is formed over substantially half the outer surface of said insulating beads on the opposite side to said substrate, an optical system for irradiating said free electron metal microparticle layer with light at a predetermined angle and detecting the irradiated light reflected from said free electron metal microparticle layer, and means for supplying a sample solution to said free electron metal microparticle layer.

6. A measuring apparatus according to claim 5, wherein the optical system for detecting said reflected irradiated light detects a spectral variation of the light.

7. A measuring apparatus according to claim 5, wherein the optical system for detecting said reflected irradiated light detects a reflectance variation of the light.

8. A measuring apparatus according to claim 5, wherein said free electron metal microparticle layer is modified by a molecule which selectively combines with a specific entity in said sample solution.

9. A measuring apparatus according to claim 6, wherein said free electron metal microparticle layer is modified by a molecule which selectively combines with a specific entity in said sample solution.

10. A measuring apparatus according to claim 7, wherein said free electron metal microparticle layer is modified by a molecule which selectively combines with a specific entity in said sample solution.

11. A measuring apparatus according to claim 8, wherein the modification of said free electron metal microparticle layer is performed by an antibody, a protein including a receptor or a nucleic acid including DNA having the ability to selectively combine with said specific entity.

12. A measuring apparatus according to claim 9, wherein the modification of said free electron metal microparticle layer is performed by an antibody, a protein including a receptor or a nucleic acid including DNA having the ability to selectively combine with said specific entity.

13. A measuring apparatus according to claim 10, wherein the modification of said free electron metal microparticle layer is performed by an antibody, a protein including a receptor or a nucleic acid including DNA having the ability to selectively combine with said specific entity.

14. A measuring apparatus comprising plural independent sensors each comprising a flat substrate and a layer of insulating beads of a polymer or non-metal arranged effectively uniformly on said substrate, wherein a thin free electron metal microparticle layer is formed over substantially half the outer surface of said insulating beads on the opposite side to the substrate, plural optical systems for irradiating said free electron metal microparticle layers of said plural independent sensors with light at a predetermined angle and detecting the irradiated light reflected from said free electron metal microparticle layers, and plural independent means for supplying sample solutions to said free electron metal microparticle layers of said plural independent sensors.

15. A measuring apparatus according to claim 14, wherein said means for supplying said sample solutions is solution aspirating means connected to said sensors, and said means uses a volume change of a space due to a piezoelectric effect of a piezo device.

16. A measuring apparatus according to claim 14, wherein the optical system for detecting said reflected irradiated light detects a spectral variation of the light.

17. A measuring apparatus according to claim 14, wherein the optical system for detecting said reflected irradiated light detects a reflectance variation of the light.

18. A measuring apparatus according to claim 14, wherein said free electron metal microparticle layer is modified by a molecule which selectively combines with a specific entity in said sample solution.

19. A measuring apparatus according to claim 16, wherein said free electron metal microparticle layer is modified by a molecule which selectively combines with a specific entity in said sample solution.

20. A measuring apparatus according to claim 17, wherein said free electron metal microparticle layer is modified by a molecule which selectively combines with a specific entity in said sample solution.

21. A measuring apparatus according to claim 18, wherein the modification of said free electron metal microparticle layer is performed by an antibody, a protein including a receptor or a nucleic acid including DNA having the ability to selectively combine with said specific entity.

22. A measuring apparatus according to claim 18, wherein the modification of said free electron metal microparticle layer is performed by an antibody, a protein including a receptor or a nucleic acid including DNA having the ability to selectively combine with said specific entity.

23. A measuring apparatus according to claim 18, wherein the modification of said free electron metal microparticle layer is performed by an antibody, a protein including a receptor or a nucleic acid including DNA having the ability to selectively combine with said specific entity.

* * * * *